US012805938B2

(12) United States Patent
Jeong et al.

(10) Patent No.: US 12,805,938 B2
(45) Date of Patent: Nov. 24, 2026

(54) METHOD FOR DETERMINING SEPARATING PLANE FOR SEPARATING ANEURYSM FROM PARENT ARTERY AND ELECTRONIC DEVICE THEREOF

(71) Applicant: Medipixel, Inc., Seoul (KR)

(72) Inventors: Eunjin Jeong, Seoul (KR); Donggyu Kim, Seoul (KR); Yeongjun Kim, Seoul (KR); Donghyun Won, Seoul (KR)

(73) Assignee: Medipixel, Inc., Seoul (KR)

( * ) Notice: Subject to any disclaimer, the term of this patent is extended or adjusted under 35 U.S.C. 154(b) by 170 days.

(21) Appl. No.: 18/822,868

(22) Filed: Sep. 3, 2024

(65) Prior Publication Data

US 2025/0072971 A1 Mar. 6, 2025

(30) Foreign Application Priority Data

Sep. 6, 2023 (KR) ........................ 10-2023-0118083
Jul. 3, 2024 (KR) ........................ 10-2024-0087635

(51) Int. Cl.
*A61B 34/10* (2016.01)
*G06T 7/00* (2017.01)
*G16H 20/40* (2018.01)

(52) U.S. Cl.
CPC ............ *A61B 34/10* (2016.02); *G06T 7/0014* (2013.01); *G16H 20/40* (2018.01);
(Continued)

(58) Field of Classification Search
CPC .............. A61B 34/10; A61B 2034/105; A61B 2034/107; G06T 7/0014;
(Continued)

(56) References Cited

U.S. PATENT DOCUMENTS 8,781,194 B2 7/2014 Malek
9,025,007 B1 5/2015 Parsons
(Continued)

FOREIGN PATENT DOCUMENTS

CN 109924956 A * 6/2019
CN 113822923 A * 12/2021 ............. G06N 3/045
(Continued)

OTHER PUBLICATIONS

Cárdenes R, Pozo JM, Bogunovic H, Larrabide I, Frangi AF. Automatic aneurysm neck detection using surface Voronoi diagrams. IEEE transactions on medical imaging. May 27, 2011;30(10):1863-76. (Year: 2011).*
(Continued)

*Primary Examiner* — Fayyaz Alam
(74) *Attorney, Agent, or Firm* — Dinsmore & Shohl LLP; Yongsok Choi, Esq.

(57) ABSTRACT

Provided is a method for determining a separating plane for separating aneurysm from a parent artery to obtain precise size information of an aneurysm. The method includes generating an aneurysm region including: generating a vessel mesh; generating a centerline based on the vessel mesh; generating a parent artery mesh based on the centerline; and generating a separating plane based on the parent artery mesh to obtain the aneurysm region.

19 Claims, 17 Drawing Sheets

(52) U.S. Cl.
CPC ... *A61B 2034/105* (2016.02); *A61B 2034/107* (2016.02); *G06T 2207/30104* (2013.01)

(58) Field of Classification Search
CPC . G06T 2207/30104; G06T 2207/30101; G06T 7/12; G06T 2207/30172; G16H 20/40
See application file for complete search history.

(56) References Cited

U.S. PATENT DOCUMENTS

| | | | | |
|---|---|---|---|---|
| 10,814,045 | B2 * | 10/2020 | Takahashi | A61B 17/1214 |
| 10,849,583 | B2 | 12/2020 | Maeda | |
| 11,779,225 | B2 * | 10/2023 | Adiyoso | A61B 5/029<br>600/301 |
| 2005/0265601 | A1 | 12/2005 | Cathier | |
| 2015/0245776 | A1 | 9/2015 | Hirohata | |
| 2018/0336676 | A1 | 11/2018 | Dutta | |
| 2020/0013218 | A1 | 1/2020 | Hatanaka | |
| 2021/0015373 | A1 | 1/2021 | Smiricinschi | |
| 2021/0224980 | A1 | 7/2021 | Yang | |

FOREIGN PATENT DOCUMENTS

| | | | | |
|---|---|---|---|---|
| CN | 116503436 | A | 7/2023 | |
| EP | 4495878 | A1 * | 1/2025 | G06T 7/0012 |
| KR | 10-2016-0114142 | A | 10/2016 | |
| KR | 10-2017-0098642 | A | 8/2017 | |
| KR | 10-2023-0096395 | A | 6/2023 | |
| KR | 10-2563710 | B1 | 8/2023 | |

OTHER PUBLICATIONS

Kimberley M, et al., “Future Unruptured Intracranial Aneurysm Growth Prediction using Mesh Convolutional Neural Networks”, Aug. 25, 2022.
Niemann, A., et al., Deep learning-based semantic vessel graph extraction for intracranial aneurysm rupture risk management. Int J CARS 18, pp. 517-525 (2023).
Bizjak, Z., et al., Vascular Surface Segmentation for Intracranial Aneurysm Isolation and Quantification.
Piccinelli, Marina et al., “Automatic Neck Plane Detection and 3D Geometric Characterization of Aneurysmal Sacs,” Annals of Biomedical Engineering, vol. 40, No. 10, pp. 2188-2214, Oct. 2012.

* cited by examiner

METHOD FOR DETERMINING SEPARATING PLANE FOR SEPARATING ANEURYSM FROM PARENT ARTERY AND ELECTRONIC DEVICE THEREOF

CROSS-REFERENCE TO RELATED APPLICATIONS

This application claims priority to and the benefit thereof under 35 U.S.C. § 119 to Korean Patent Application No. 10-2023-0118083 filed in the Korean Intellectual Property Office on Sep. 6, 2023, and Korean Patent Application No. 10-2024-0087635 filed in the Korean Intellectual Property Office on Jul. 3, 2024, the entire contents of which are incorporated herein by reference.

BACKGROUND

(a) Field

The disclosure relates to a method for determining a separating plane for separating aneurysm from a parent artery and an electronic device thereof.

(b) Description of the Related Art

An aneurysm is a disease where part of an artery wall weakens and balloons out, which can occur in various forms such as cerebral aneurysm, aortic aneurysm, renal artery aneurysm, and splenic artery aneurysm. Among the treatment methods for aneurysms, coil embolization is a prominent technique where a thin coil is inserted into the aneurysm to block the flow of blood into the cerebral aneurysm.

To perform coil embolization effectively, it is crucial to accurately measure the size of the aneurysm, including volume and length, as these measurements are used to determine the appropriate amount of coil needed. Traditionally, medical professionals estimated the size of the aneurysm by analyzing images and using polyhedral shapes, like octagons, to approximate the size. However, there is an increasing demand for methods that can determine the size more precisely, ensuring it matches the actual shape of the aneurysm.

SUMMARY

Some embodiments may provide a method for determining a separating plane for separating aneurysm from a parent artery and an electronic device thereof to obtain precise size information of an aneurysm.

According to an aspect of an embodiment, a method for generating an aneurysm region may include: generating a vessel mesh; generating a centerline based on the vessel mesh; generating a parent artery mesh based on the centerline; and generating a separating plane based on the parent artery mesh to obtain the aneurysm region.

According to an aspect of an embodiment, an electronic device may include a processor; and a memory connected to the processor, wherein the memory is configured to store a program, the processor is configured to execute the program, and when the program is executed, the steps of a method for generating an aneurysm region are implemented.

Additional aspects may be set forth in part in the description which follows and, in part, may be apparent from the description, and/or may be learned by practice of the presented embodiments.

BRIEF DESCRIPTION OF THE DRAWINGS

The above and other aspects, features, and advantages of certain embodiments of the present disclosure will become apparent from the following description taken in conjunction with the accompanying drawings, in which.

DETAILED DESCRIPTION OF THE INVENTION

Figure 1:
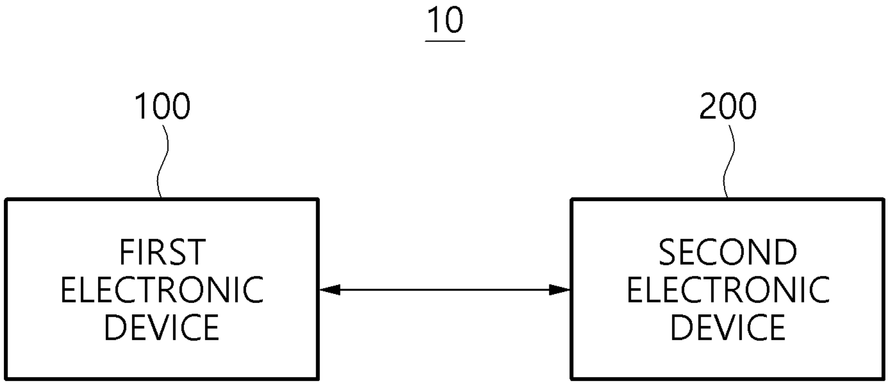
FIG. 1 is a schematic block diagram of the computing system according to an embodiment.

In the following detailed description, only certain embodiments of the present invention have been shown and described, simply by way of illustration. As those skilled in the art would realize, the described embodiments may be modified in various different ways, all without departing from the spirit or scope of the present invention.

The drawings and description are to be regarded as illustrative in nature and not restrictive. Like reference numerals designate like elements throughout the specification. The sequence of operations or steps is not limited to the order presented in the claims or figures unless specifically indicated otherwise. The order of operations or steps may be changed, several operations or steps may be merged, a certain operation or step may be divided, and a specific operation or step may not be performed.

As used herein, the singular forms "a" and "an" are intended to include the plural forms as well, unless the context clearly indicates otherwise. Although the terms first, second, and the like may be used herein to describe various elements, components, steps and/or operations, these terms are only used to distinguish one element, component, step or operation from another element, component, step, or operation.

As used herein, each of such phrases as "A or B," "at least one of A and B," "at least one of A or B," "A, B, or C," "at least one of A, B, and C," and "at least one of A, B, or C," may include any possible combination of the items enumerated together in a corresponding one of the phrases.

Reference throughout the present disclosure to "one embodiment," "an embodiment," "an example embodiment," or similar language may indicate that a particular feature, structure, or characteristic described in connection with the indicated embodiment is included in at least one embodiment of the present solution. Thus, the phrases "in one embodiment", "in an embodiment," "in an example embodiment," and similar language throughout this disclosure may, but do not necessarily, all refer to the same embodiment.

Hereinafter, various embodiments of the present disclosure are described with reference to the accompanying drawings.

Figure 2:
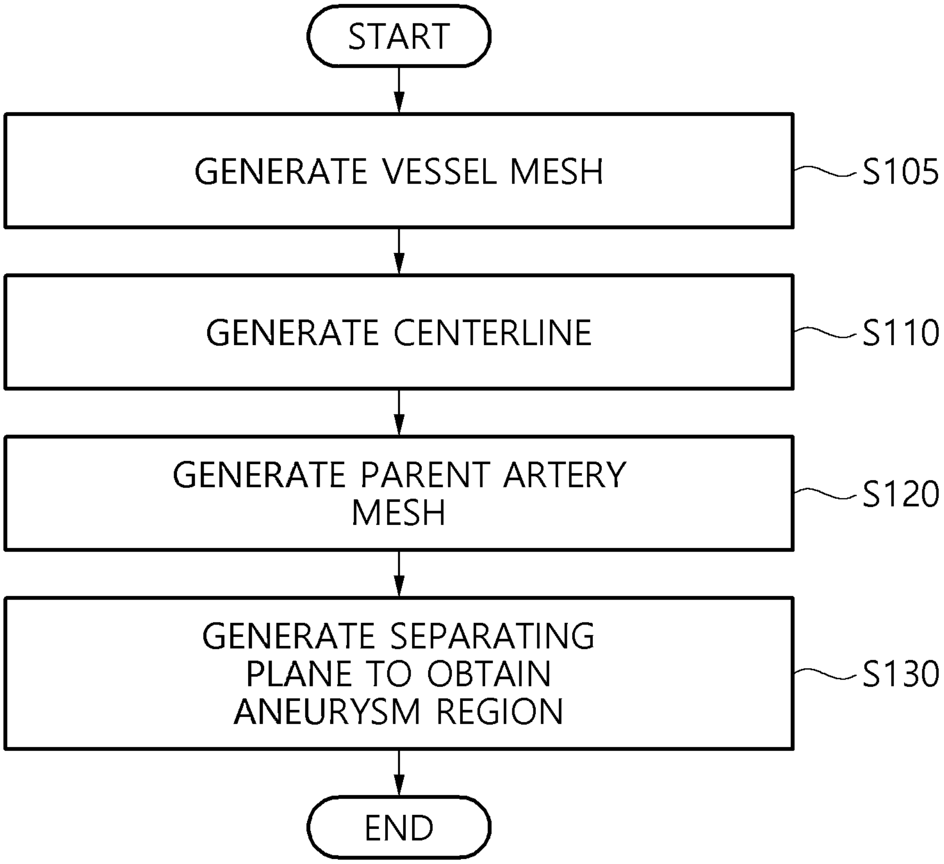
FIG. 2 is an example flowchart showing a method for generating aneurysm region according to an embodiment.

FIG. 1 is a schematic block diagram of the computing system according to an embodiment, and FIG. 2 is an example flowchart showing a method for generating aneurysm region according to an embodiment.

Referring to FIG. 1, a computing system 10 according to an embodiment may obtain a vessel image of a first user, perform image processing on the obtained vessel image, and display the processed image. The computing system 10 may provide the processed image to a second user. For example, the first user may be a patient, and the second user may be a medical professional.

In some embodiments, the computing system 10 may capture a brain vascular of the first user to obtain a brain vascular image and generate an aneurysm region by performing image processing on the brain vascular image. However, the embodiments are not limited thereto, and the computing system 10 may capture blood vessels that are the subject of angiography, such as the cardiovascular system or gastrointestinal vessels.

The computing system 10 according to an embodiment includes a first electronic device 100 and a second electronic device 200. The first electronic device 100 may be an imaging device that captures an image of the first user to obtain an image. For example, the first electronic device 100 may be an angiography equipment (for example, angiodevice), Optical Coherence Tomography (OCT) equipment, Computed Tomography (CT) equipment, Magnetic Resonance Imaging (MRI) equipment, or Magnetic Resonance Angiography (MRA) equipment.

The first electronic device 100 may capture the first user from multiple imaging points to obtain the plurality of images. In some embodiments, the first electronic device 100 may capture the first user while rotating around the first user. In other embodiments, the first electronic device 100 may rotate the first user and capture the first user while rotating. The first electronic device 100 may transmit the obtained images to the second electronic device 200.

The second electronic device 200 may be a computing device performing image processing on a plurality of images received from the first electronic device 100. The second electronic device 200 may generate an aneurysm region based on the plurality of images.

The second electronic device 200 may perform a method for generating an aneurysm region shown in FIG. 2. The second electronic device 200 may include a memory that stores a program for executing the method for generating the aneurysm region and a processor configured to execute the program to generate the aneurysm region. The second electronic device 200 may further include input/output devices (such as input devices like a mouse or keyboard, output devices like a display panel, and input/output devices like a touchscreen panel, etc.), communication devices, and others.

Referring to FIGS. 1 and 2, the second electronic device 200 may generate a vessel mesh (S105). The second electronic device 200 may receive a plurality of images captured by the first electronic device 100. The second electronic device 200 may generate the vessel mesh by applying marching cube algorithm to the plurality of images. The vessel mesh may be data representing blood vessels in three dimensions.

The second electronic device 200 may generate a centerline within the vessel mesh (S110). The second electronic device 200 may generate a voronoi diagram based on the vessel mesh. The second electronic device 200 may generate a plurality of inscribed spheres within the vessel mesh based on the voronoi diagram. The voronoi diagram may define points associated with the vessel mesh, the radius of the inscribed spheres, and the like. The second electronic device 200 may determine points where the sum of the radii of the plurality of inscribed spheres is maximized and may determine a line connecting the points as the centerline. The points may represent the centers of the inscribed spheres. In some embodiments, the second electronic device 200 may generate the centerline using VMTK (Vascular Modeling Toolkit) library.

The centerline may include a vessel centerline that connects blood vessels and an aneurysm centerline that connects an aneurysm to a blood vessel. Specifically, when a first open vessel is the start point and a second open vessel is the end point, the second electronic device 200 may determine points where the sum of the radii of the inscribed spheres between the first open vessel and the second open vessel is maximized as the vessel centerline. When the aneurysm is the start point and an open vessel is the end point, the second electronic device 200 may determine points where the sum of the radii of the inscribed spheres between the aneurysm and the open vessel is maximized as the aneurysm centerline. The second electronic device 200 may perform interpolation when generating the centerline by connecting the points. The configuration of generating the vessel centerline and the aneurysm centerline by the second electronic device 200 will be described with reference to FIGS. 3 to 6.

The second electronic device 200 may generate a parent artery mesh (S120). The parent artery mesh may be data estimating the appearance of a normal blood vessel under the assumption that the aneurysm does not exist. The second electronic device 200 may generate a tube mesh based on the vessel centerline. The tube mesh may be defined based on the vessel centerline and the radius of the vessel centerline. The second electronic device 200 may determine an aneurysm entry point based on the tube mesh and the aneurysm centerline. The second electronic device 200 may determine a point on the vessel centerline that is closest to the aneurysm entry point as a slice point. The second electronic device 200 may divide the vessel centerline based on the slice point. The divided vessel centerlines may be referred to as a first vessel centerline and a second vessel centerline, respectively.

The second electronic device 200 may determine a first clipping point on the first vessel centerline and a second clipping point on the second vessel centerline. The clipping points may represent the boundaries of the aneurysm region. For example, the aneurysm region may begin at the first clipping point and may end at the second clipping point.

The second electronic device 200 may perform interpolation based on the first and second clipping points. In some embodiments, the second electronic device 200 may generate a spline curve by applying a spline method to the first and second clipping points and at least one adjacent point. For example, the spline method may be a tension-based spline, and the embodiment is not limited thereto. The second electronic device 200 may generate the parent artery mesh based on the spline curve. The configuration of generating the parent artery mesh by the second electronic device 200 will be described with reference to FIGS. 7 to 12.

The second electronic device 200 may generate a separating plane to obtain the aneurysm region (S130). The second electronic device 200 may determine separating plane candidates based on one of the points inside or outside the parent artery mesh and one of candidate vectors. The candidate vectors may refer to vectors adjacent to an aneurysm vector defined by the aneurysm entry point and the slice point. For example, the candidate vectors may have an angle with the aneurysm vector that is equal to or less than (or less than) a predetermined angle.

The second electronic device 200 may calculate scores of the separating plane candidates and determine the separating plane based on the scores. In some embodiments, the second electronic device 200 may determine the separating plane candidate with a score greater than or equal to (or greater than) a predetermined value as the separating plane. In some embodiments, the second electronic device 200 may determine the separating plane candidate with the highest score as the separating plane. The configuration of generating the separating plane by the second electronic device 200 will be described with reference to FIGS. 13 to 16.

The second electronic device 200 may be a server, a data center, an Artificial Intelligence (AI) device, a Personal Computer (PC), a laptop computer, a mobile phone, a smart phone, a tablet PC, a wearable device, a healthcare device, etc.

In some embodiments, when the second electronic device 200 is implemented as a server, data center, or similar system, the computing system 10 may further include a third electronic device for interacting with the second user. For example, the third electronic device may interact with the second user by displaying images and receiving input from the second user. The third electronic device may communicate with the first electronic device and/or the second electronic device.

Figure 3:
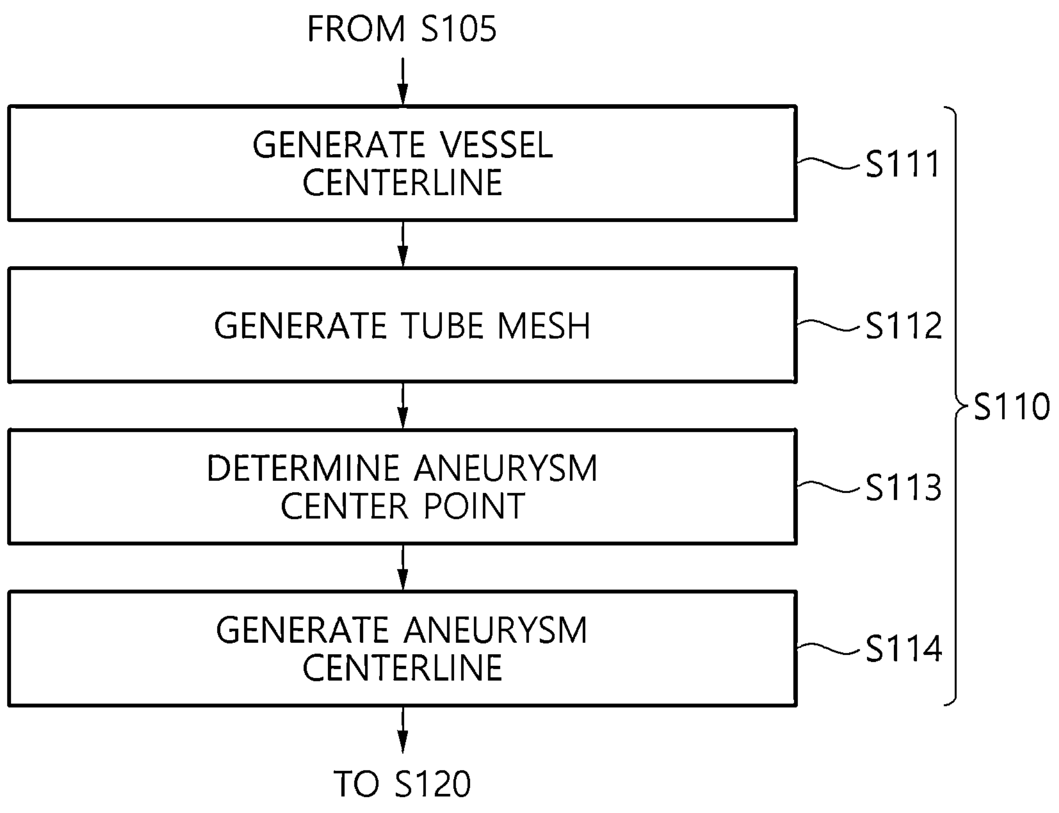
FIG. 3 is a flowchart illustrating a method for generating a centerline according to an embodiment.
Figure 4:
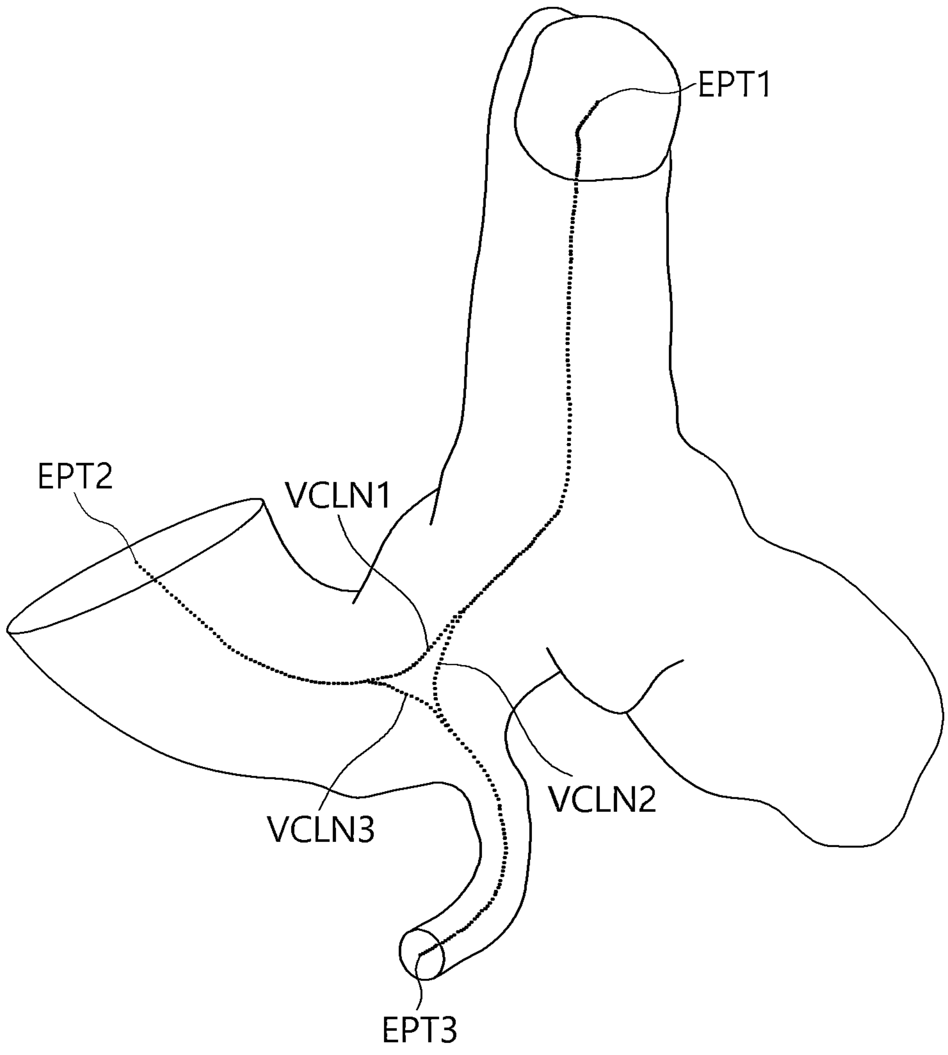
FIGS. 4 to 6 illustrate a method for generating a centerline by an electronic device according to an embodiment.
Figure 5:
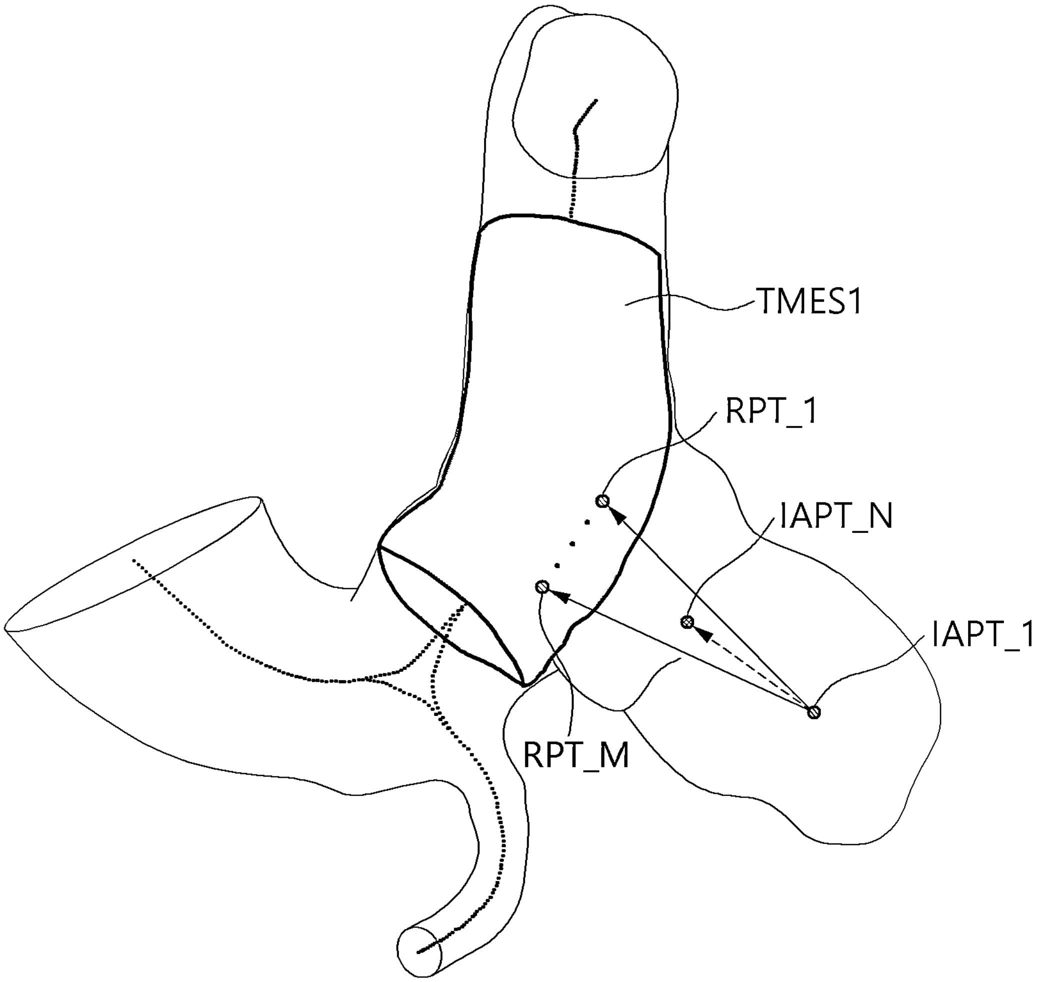
Figure 6:
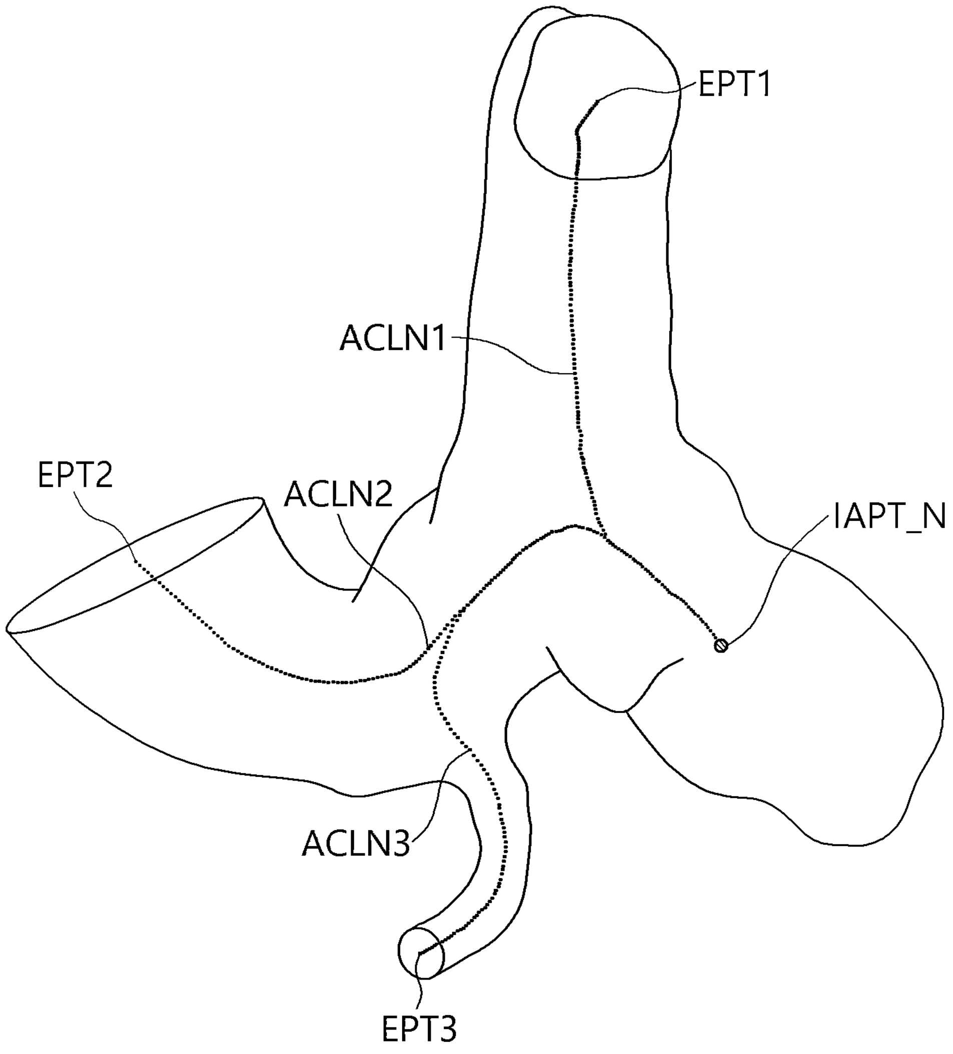

FIG. 3 is a flowchart illustrating a method for generating a centerline according to an embodiment, and FIGS. 4 to 6 illustrate a method for generating a centerline by an electronic device according to an embodiment.

Referring to FIG. 3, an electronic device (e.g., 200 in FIG. 1) according to an embodiment may generate a vessel centerline (S111). The electronic device may generate a vessel mesh and may generate the vessel centerline.

The electronic device may detect an open vessel within the vessel mesh. The open vessel may refer to a blood vessel that is not occluded. The electronic device may generate a vessel centerline that reaches from one open vessel to another open vessel in the vessel mesh. The electronic device may generate a plurality of inscribed spheres along the path from one open vessel to another open vessel. The electronic device may generate the inscribed spheres so that the sum of the radii of the inscribed spheres is maximized, and may generate the vessel centerline by connecting center points of the inscribed spheres.

Referring to FIGS. 3 and 4, the vessel mesh may include a plurality of open vessels. For example, the vessel mesh may include a first open vessel, a second open vessel, and a third open vessel. The electronic device may generate a first vessel centerline (VCLN1) connecting a center point (EPT1) of the first open vessel to a center point (EPT2) of the second open vessel, a second vessel centerline (VCLN2) connecting the center point (EPT1) of the first open vessel to a center point (EPT3) of the third open vessel, and a third vessel centerline (VCLN3) connecting the center point (EPT2) of the second open vessel to the center point (EPT3) of the third open vessel.

The electronic device may generate a tube mesh (S112). The electronic device may generate the tube mesh based on the inscribed spheres of the vessel centerlines (VCLN1 to VCLN3). For example, the electronic device may generate the tube mesh based on the center points of the vessel centerlines (VCLN1 to VCLN3) and radius information corresponding to each of the center points. In FIG. 5, a part of the tube mesh is illustrated as TMES1.

Referring to FIGS. 3 to 5, the electronic device may determine an aneurysm center point (IAPT_N) (S113). The electronic device may determine the aneurysm center point (IAPT_N) based on an aneurysm point (IAPT_1) and the tube mesh (TMES1). In some embodiments, the electronic device may determine the aneurysm point (IAPT_1) based on user input. In some embodiments, the electronic device may determine the aneurysm point (IAPT_1) using an artificial neural network trained to output an aneurysm point (for example, IAPT_1) from the vessel mesh. In some embodiments, the artificial neural network may be trained to output an aneurysm center point (for example, IAPT_N) from the vessel mesh.

The electronic device may generate a plurality of first rays within the vessel mesh, starting from the aneurysm point (IAPT_1) as a start point. The electronic device may determine first points (RPT_1 to RPT_M, where M is an integer greater than 1) where the plurality of first rays intersect with the first tube mesh (TMES1).

The electronic device may determine the aneurysm center point (IAPT_N) based on the first points (RPT_1 to RPT_M). For example, the electronic device may determine the center of the aneurysm point (IAPT_1) and the first points (RPT_1 to RPT_M) as a first center point. The electronic device may generate a plurality of second rays within the vessel mesh, starting from the first center point as a start point. The electronic device may determine the second points where the plurality of second rays intersect with the tube mesh (TMES1).

The electronic device may determine the center of the first center point and the second points as a second center point. If the distance between the first center point and the second center point is less than (or less than or equal to) a predetermined distance, the electronic device may determine the second center point as the aneurysm center point (IAPT_N).

If the distance between the first center point and the second center point is greater than or equal to the predetermined distance, the electronic device may determine a third center point based on the second center point. If the distance between the second center point and the third center point is less than the predetermined distance, the electronic device may determine the third center point as the aneurysm center point (IAPT_N). In this manner, the electronic device may continue to determine a center point until the distance between a previous center point and a current center point is less than the predetermined distance.

The electronic device may generate an aneurysm centerline (S114). The electronic device may generate the aneurysm centerline based on an open vessel and the aneurysm center point (IAPT_N). The electronic device may generate an aneurysm centerline extending from one open vessel to the aneurysm center point (IAPT_N) in the vessel mesh. The electronic device may generate a plurality of inscribed spheres along the path from one open vessel to the aneurysm center point (IAPT_N). The electronic device may generate the inscribed spheres so that the sum of the radii of the inscribed spheres is maximized and may generate the aneurysm centerline by connecting center points of the inscribed spheres.

Referring to FIGS. 3 to 6, the electronic device may generate a first aneurysm centerline (ACLN1) connecting the center point (EPT1) of the first open vessel to the aneurysm center point (IAPT_N), a second aneurysm centerline (ACLN2) connecting the center point (EPT2) of the second open vessel to the aneurysm center point (IAPT_N), and a third aneurysm centerline (ACLN3) connecting the center point (EPT3) of the third open vessel to the aneurysm center point (IAPT_N). The electronic device may generate the aneurysm centerlines (ACLN1 to ACLN3) (S114) and generate the parent artery mesh (S120).

In FIG. 3, although the steps (S111 to S114) are illustrated as being included in step (S110) of FIG. 2, step (S110) may be modified to include additional steps or omit certain steps. For example, step (S110) may be implemented to include steps (S111 and S114). In this case, the electronic device may use an artificial neural network trained by using a training dataset with the vessel centerline as input data and the aneurysm centerline as output data.

In another example, step (S110) may be implemented to include steps (S111, S113, and S114). In this case, the electronic device may use an artificial neural network trained by using a training dataset with the vessel centerline as input data and the aneurysm center point as output data.

Figure 7:
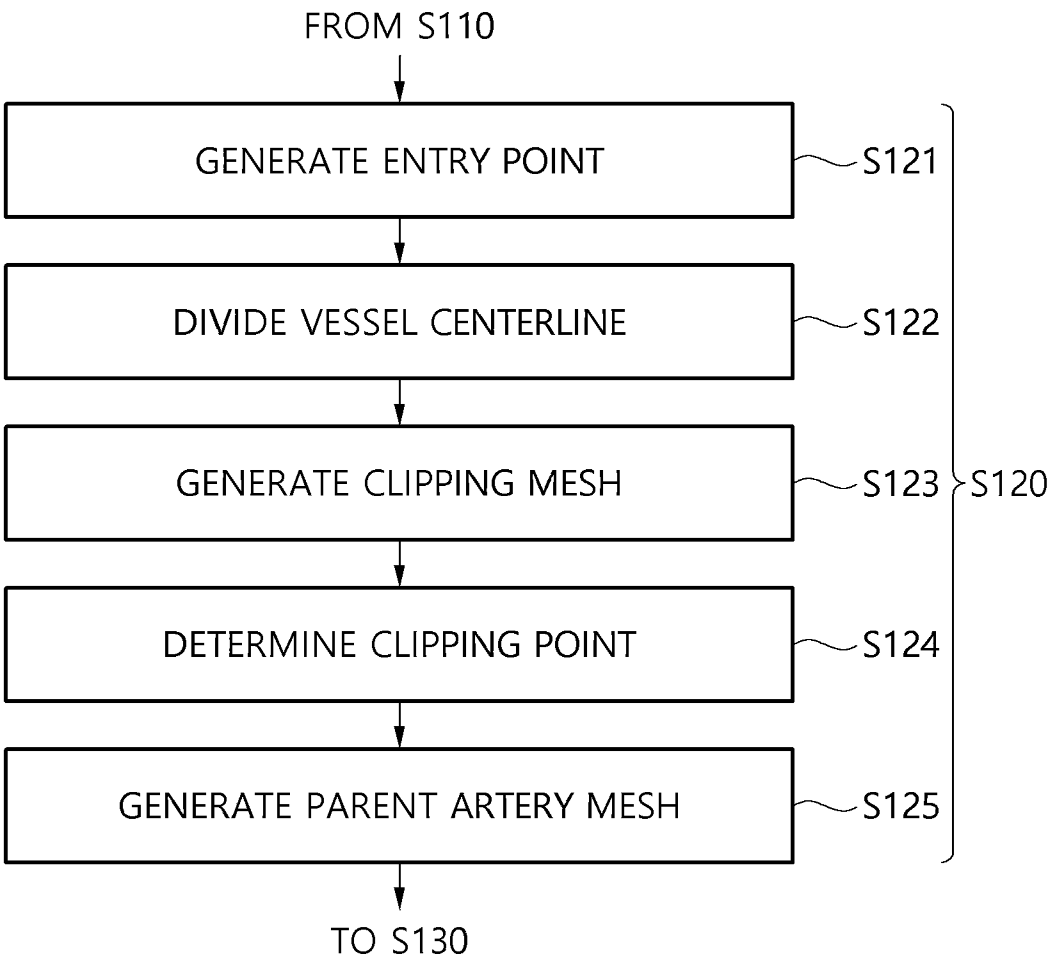
FIG. 7 is a flowchart illustrating a method for generating a parent artery mesh according to an embodiment.

FIG. 7 is a flowchart illustrating a method for generating a parent artery mesh according to an embodiment, and FIGS. 8 to 12 illustrate a method for generating a parent artery mesh by an electronic device according to an embodiment.

Referring to FIG. 7, an electronic device (e.g., 200 in FIG. 1) according to an embodiment may generate a centerline (S110) and may generate an entry point (S121). The entry point may refer to a point where a blood vessel leads into an aneurysm. The entry point may be one of points on the centerline. For example, the electronic device may generate the entry point based on the aneurysm centerline.

Figure 8:
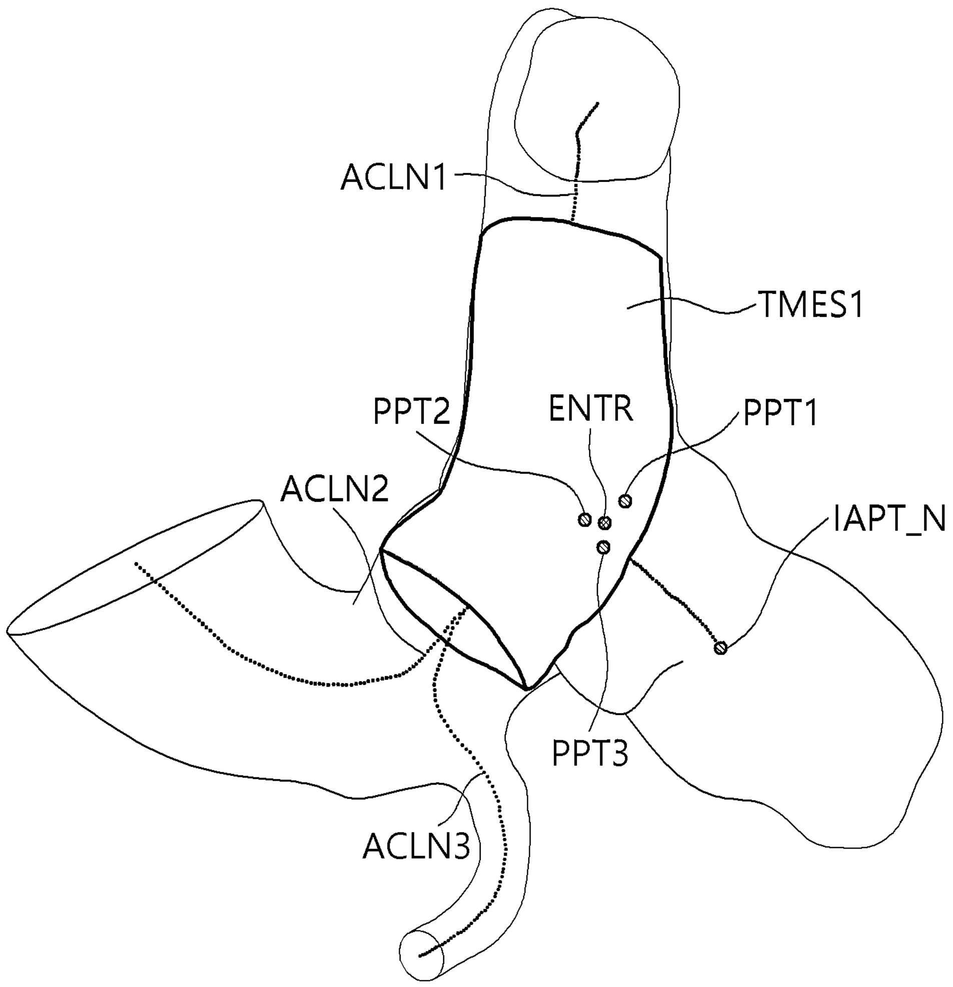
FIGS. 8 to 12 illustrate a method for generating a parent artery mesh by an electronic device according to an embodiment.

Referring to FIGS. 7 and 8, the electronic device may determine an entry point (ENTR) based on aneurysm centerlines (ACLN1 to ACLN3) and the tube mesh (TMES1). The aneurysm centerlines (ACLN1 to ACLN3) may be explained in the same manner as described with reference to FIG. 6, and redundant details are omitted. The electronic device may determine first points (PPT1 to PPT3) where the aneurysm centerlines (ACLN1 to ACLN3) intersects with the tube mesh (TMES1). That is, the aneurysm centerlines (ACLN1 to ACLN3) may pass through the tube mesh (TMES1) at the first points (PPT1 to PPT3). The electronic device may determine the center of the first points (PPT1 to PPT3) as the entry point (ENTR).

The electronic device may divide the vessel centerline (S122). The vessel centerline may be explained in the same manner as described with reference to FIG. 4, and redundant details are omitted. The electronic device may divide the vessel centerline based on the entry point.

Figure 9:
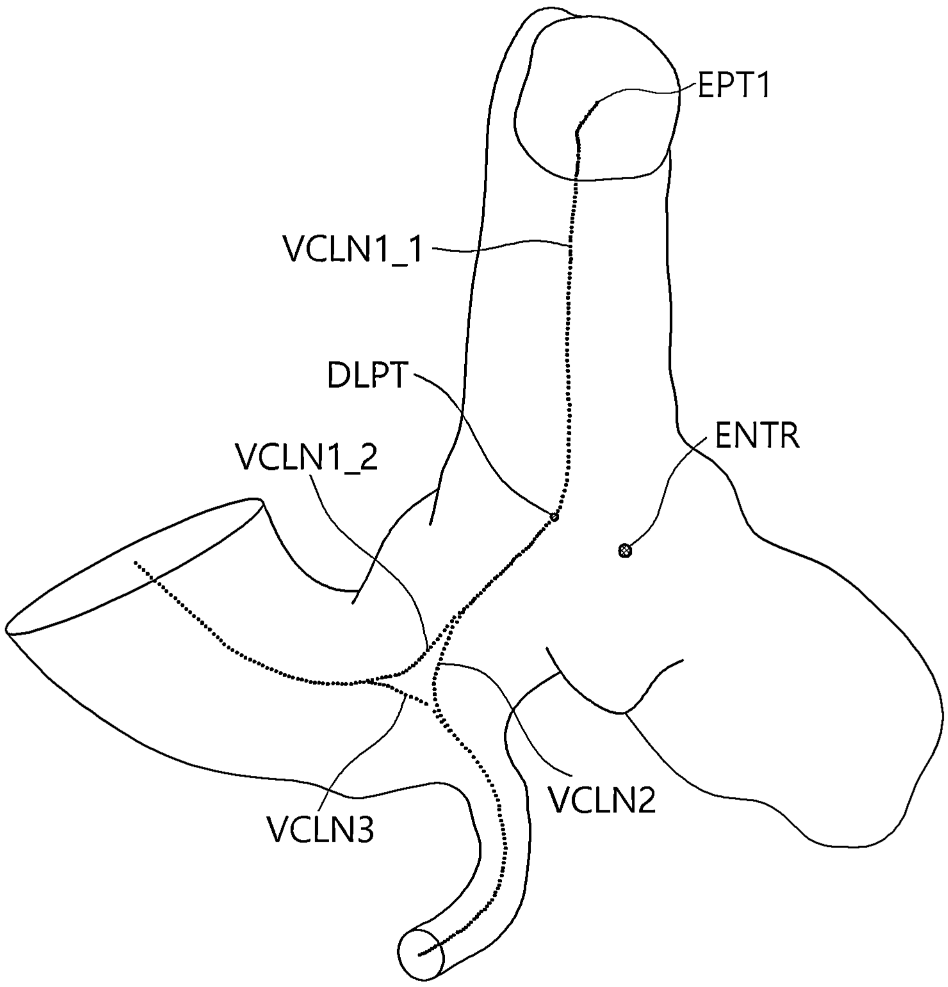

Referring to FIGS. 7 to 9, the electronic device may divide a vessel centerline (VCLN1 in FIG. 4) based on the entry point (ENTR) to obtain a first vessel centerline (VCLN1_1) and a second vessel centerline (VCLN1_2). In some embodiments, the electronic device may determine a point on the vessel centerline (VCLN1) closest to the entry point (ENTR) as a slice point (DLPT). The electronic device may divide the vessel centerline (VCLN1) based on the slice point (DLPT).

Figure 10:
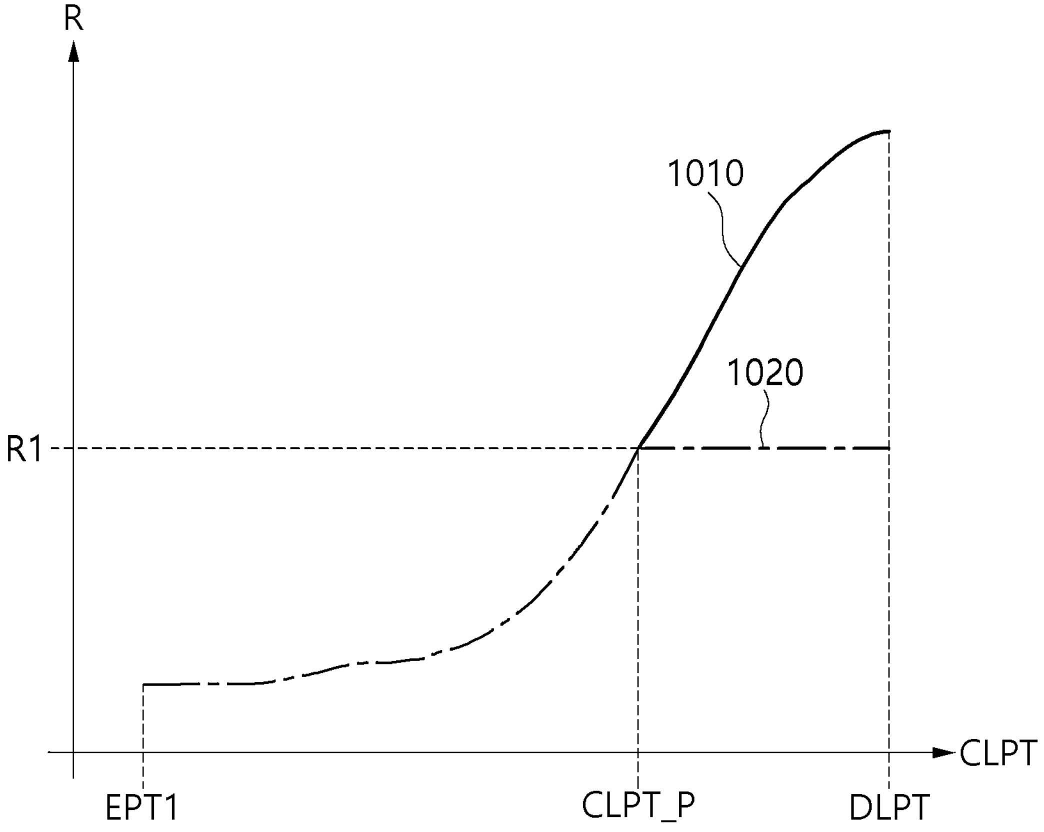

The electronic device may generate a clipping mesh (S123). The clipping mesh may be a mesh used to determine a clipping point. The electronic device may generate a first clipping mesh based on the first vessel centerline (VCLN1_1) and a second clipping mesh based on the second vessel centerline (VCLN1_2). Hereafter, with reference to FIG. 10, the configuration in which the electronic device generates the clipping mesh from the first vessel centerline (VCLN1_1) will be described. In FIG. 10, radius values (R) of center points (CLPT) of the first vessel centerline (VCLN1_1) can be observed. The radius values (R) of the center points (CLPT) may correspond to graph 1010. In the graph 1010, the radius values (R) of the center points (CLPT) of the first vessel centerline (VCLN1_1) may tend to increase as they get closer to the aneurysm. For example, a radius value (R1) at a center point (CLPT_P) may be larger than a radius value at a center point (EPT1). A radius value at a center point (DLPT) may be larger than the radius value (R1) at the center point (CLPT_P).

The electronic device may modify the radius values (R) of the center points (CLPT) based on a reference value. For example, if the radius value (R) is greater than the reference value, the electronic device may change the radius value (R) to the reference value. In some embodiments, the electronic device may determine the reference value as R1. The electronic device may change the radius values (R) of the center points from the center point (CLPT_P) to the center point (DLPT) to R1. The modified radius values (R) may correspond to the graph 1020. This adjustment can resolve the issue of overestimating the radius of the centerline near the aneurysm. Although the case where the reference value is R1 has been described, the embodiment is not limited thereto, and the reference value can be set to various values depending on the embodiment.

The electronic device may generate the clipping mesh based on the center points (CLPT) and modified radius values of the center points (CLPT). The electronic device may scale the modified radius values. For example, the electronic device may multiply the radius values by a scaling factor. Depending on the embodiment, the scaling factor can be set to various values. The electronic device may generate the clipping mesh based on the center points (CLPT) and the scaled radius values.

The electronic device may insert the clipping mesh into the vessel mesh. For example, the electronic device may insert the clipping mesh based on the vessel centerline. As the centerline of the clipping mesh corresponds to the vessel centerline, the electronic device may insert the clipping mesh by matching the centerline of the clipping mesh to the vessel centerline.

The electronic device may generate a plurality of rays from the center points (CLPT). For example, the electronic device may generate the plurality of rays radiating in the cross-sectional direction of the blood vessel. In some embodiments, the electronic device may determine a plane having a normal vector as a cross-sectional plane, where the normal vector is defined by a vector between the current center point and the previous center point (or the subsequent center point). The electronic device may generate the plurality of rays defined on the cross-sectional plane.

The electronic device may determine intersection points where the plurality of rays intersect with the vessel mesh and the clipping mesh. For example, the electronic device may determine first intersection points where the plurality of rays intersect with the vessel mesh and second intersection points where the plurality of rays intersect with the clipping mesh.

Figure 11:
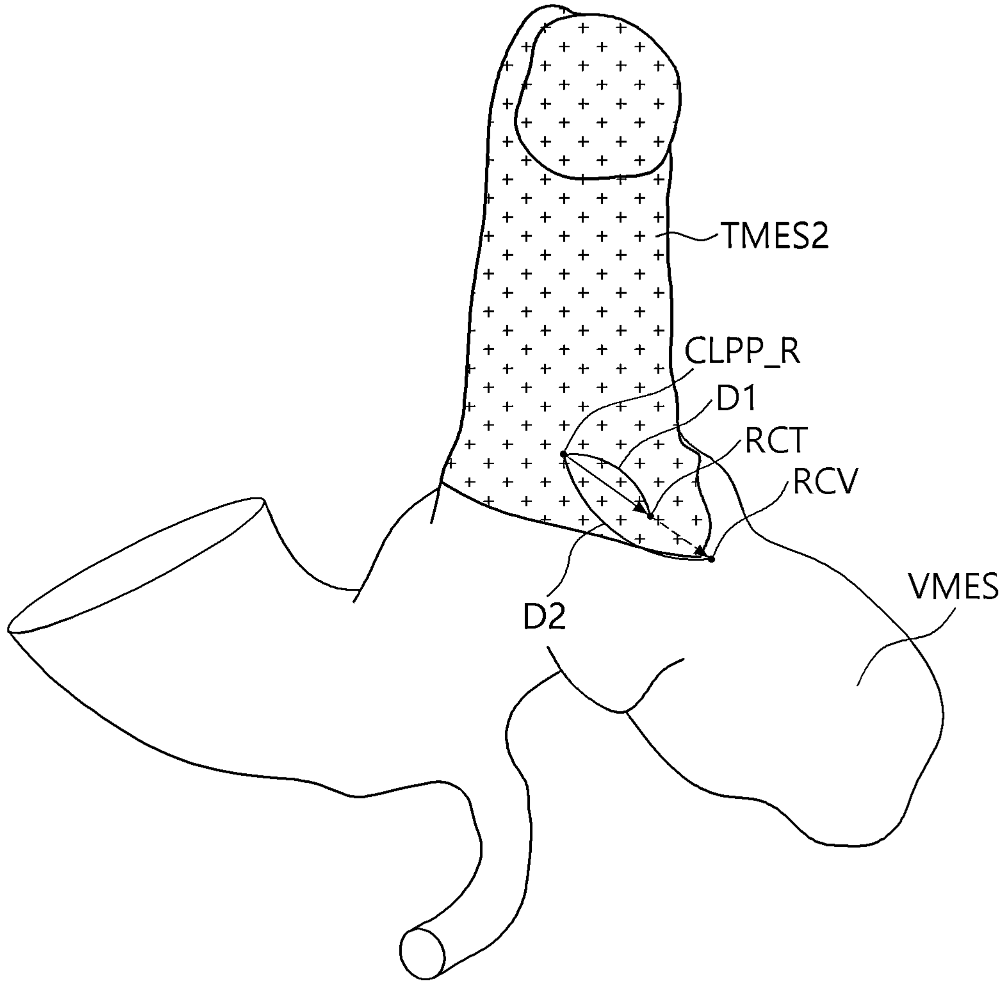

The electronic device may determine a first distance between the center points (CLPT) and the first intersection points. The electronic device may determine a second distance between the center points (CLPT) and the second intersection points. The electronic device may modify the clipping mesh based on the first and second distances. For example, the electronic device may adjust the clipping mesh to have the shorter of the two distances, ensuring a tighter fit to the vessel mesh. This means that the electronic device can obtain a clipping mesh that fits precisely to the vessel mesh. Consequently, the aneurysm region can be obtained with precision and efficiency, regardless of whether the cross-section of the blood vessel has a primitive shape like a circle or ellipse, or a more complex shape like a NURBS (non-uniform rational b-spline) surface. FIG. 11 illustrates a clipping mesh (TMES2) that fits tightly to the vessel mesh (VMES). The electronic device may generate a clipping mesh for the second vessel centerline (VCLN1_2) in the same manner.

Referring to FIGS. 7 and 11, the electronic device may determine a clipping point (S124). The clipping point may represent the boundary of the aneurysm. The electronic device may verify the center points of the clipping mesh (TMES2) as candidates for the clipping point. The electronic device may begin the verification process from a slice point (e.g., DLPT in FIG. 9) toward a center point (e.g., EPT1 in FIG. 9).

The electronic device may generate a plurality of rays originating from a clipping point candidate (CLPP_R). In some embodiments, the electronic device may generate the plurality of rays based on a first vector directed from the clipping point candidate (CLPP_R) toward an aneurysm center point (e.g., IAPT_N in FIG. 6). The electronic device may generate second vectors that have an angle with the first vector that is less than or equal to a predetermined angle. The electronic device may generate the plurality of rays corresponding to the first vector and the second vectors. While the above description explains a configuration where the first vector is generated based on the aneurysm center point, the embodiment is not limited thereto, and the electronic device may generate various vectors from the clipping point candidate (CLPP_R) toward the aneurysm.

The electronic device may determine a first intersection point (RCT) where the plurality of rays intersect with the clipping mesh (TMES2) and a second intersection point (RCV) where the plurality of rays intersect with the vessel mesh (VMES). The electronic device may perform verification based on the first intersection point (RCT) and the second intersection point (RCV). For example, the electronic device may perform verification based on a first distance (D1) between the clipping point candidate (CLPP_R) and the first intersection point (RCT) and a second distance (D2) between the clipping point candidate (CLPP_R) and the second intersection point (RCV).

The electronic device may determine that the verification of the clipping point candidate (CLPP_R) is successful if the ratio of the first distance (D1) to the second distance (D2) is greater than (or is greater than or equal to) a threshold. In other words, the electronic device may determine the clipping point candidate (CLPP_R) as the clipping point.

The electronic device may determine that the verification of the clipping point candidate (CLPP_R) has failed if the ratio of the first distance (D1) to the second distance (D2) is less than or equal to (or is less than) the threshold. The electronic device may perform verification on the subsequent clipping point candidate (e.g., CLPP_R+1).

The electronic device may use the same method to determine a clipping point for the clipping mesh of the second vessel centerline (e.g., VCLN1_2 in FIG. 9). That is, the electronic device may determine a first clipping point for the clipping mesh (TMES2) of the first vessel centerline and a second clipping point for the clipping mesh of the second vessel centerline.

Figure 12:
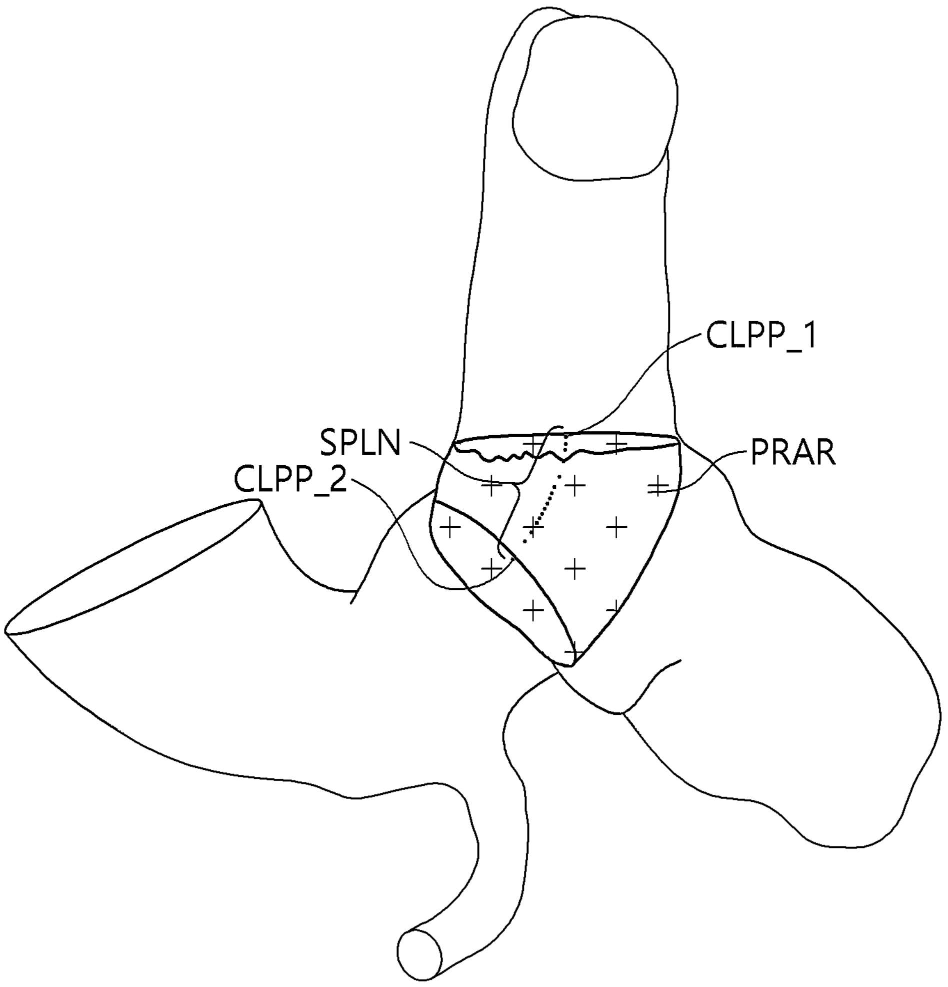

Referring to FIGS. 7 and 12, the electronic device may generate a parent artery mesh (PRAR) based on a first clipping point (CLPP_1) and a second clipping point (CLPP_2) (S125). The electronic device may perform interpolation between the clipping points (CLPP_1 and CLPP_2) to generate an interpolation centerline. For example, the electronic device may perform interpolation between the first clipping point (CLPP_1), a first center point adjacent to the first clipping point (CLPP_1) on the vessel centerline, the second clipping point (CLPP_2), and a second center point adjacent to the second clipping point (CLPP_2) on the vessel centerline. The first center point may be a point adjacent to the first clipping point (CLPP_1) in the direction outside the aneurysm boundary. The second center point may be a point adjacent to the second clipping point (CLPP_2) in the direction outside the aneurysm boundary. For example, the electronic device may use a tension-based spline to obtain a plurality of interpolation points (SPLN). The electronic device may generate the interpolation centerline based on the plurality of interpolation points (SPLN).

While the above description explains a configuration in which the electronic device performs interpolation based on the first clipping point (CLPP_1), the first center point, the second clipping point (CLPP_2), and the second center point, the embodiment is not limited thereto. For example, the electronic device may also perform interpolation based on at least two points among the first clipping point (CLPP_1), the first center point, the second clipping point (CLPP_2), and the second center point.

The clipping points (CLPP_1 and CLPP_2) and the first and second center points may have radius information, respectively. The electronic device may perform interpolation on first radius information of the clipping points (CLPP_1 and CLPP_2) and the first and second center points to generate second radius information for the interpolation centerline. The electronic device may generate the parent artery mesh (PRAR) based on the interpolation centerline and the second radius information. The electronic device may generate the parent artery mesh (PRAR) (S125), and generate a separating plane (S130).

In FIG. 7, although the steps (S121 to S125) are shown as being included in step (S120) of FIG. 2, step (S120) may be modified to include additional steps or to omit certain steps. For example, step (S120) may be implemented to include steps (S121, S124, and S125). In this case, the electronic device may use an artificial neural network trained by using a training dataset with the entry point as input data and the clipping point as output data.

Figure 13:
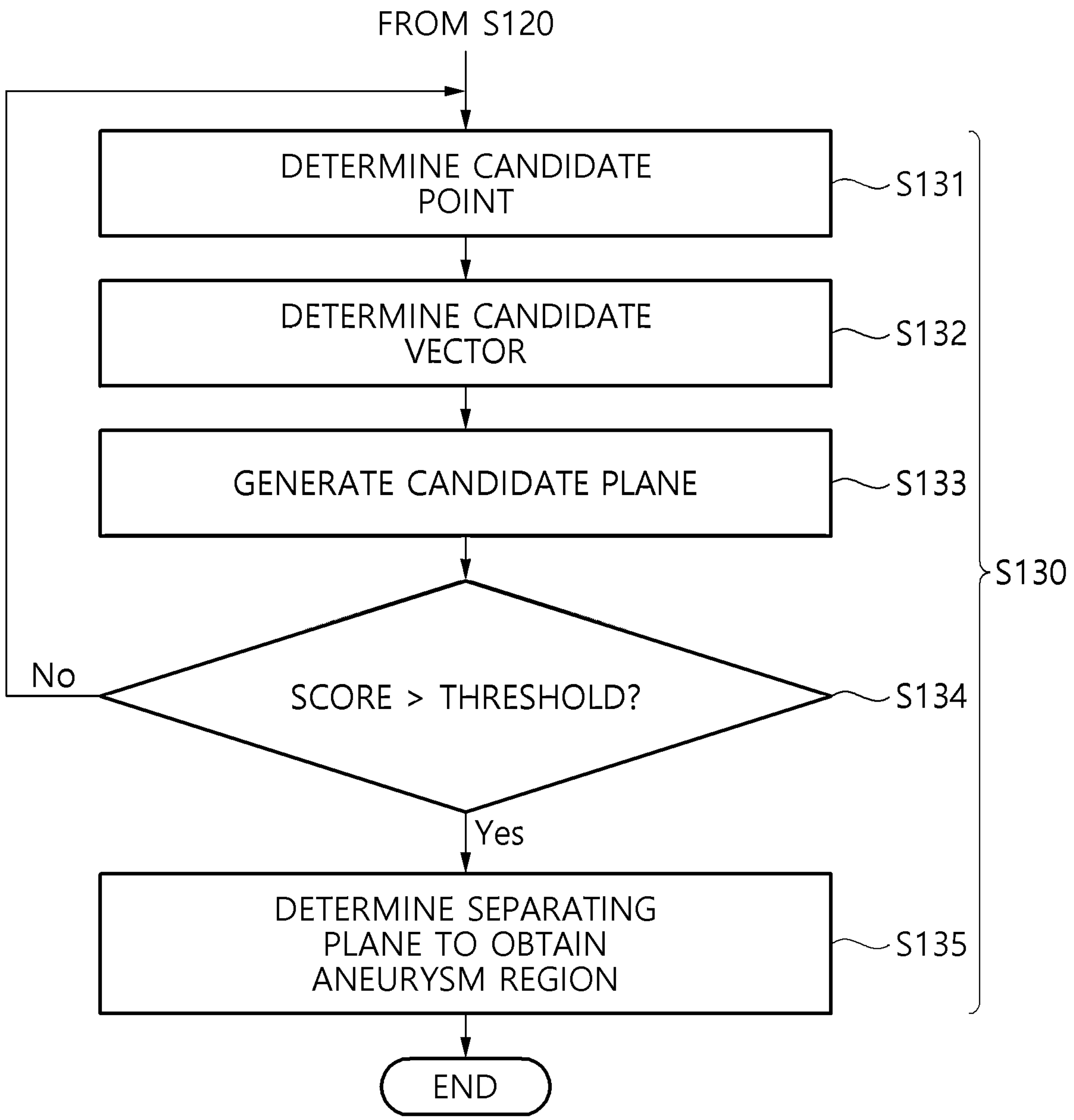
FIG. 13 is a flowchart illustrating a method for generating a separating plane according to an embodiment.
Figure 14:
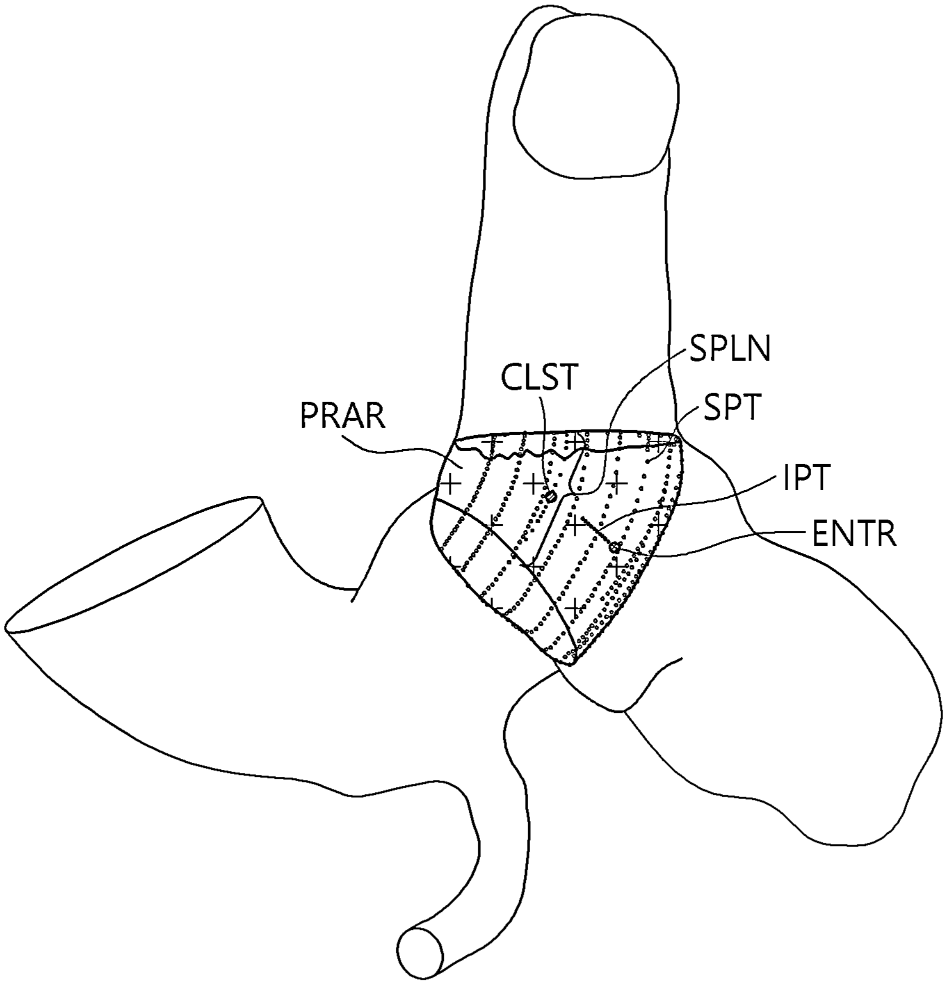
FIGS. 14 to 16 illustrate a method for generating a separating plane by an electronic device according to an embodiment.
Figure 15:
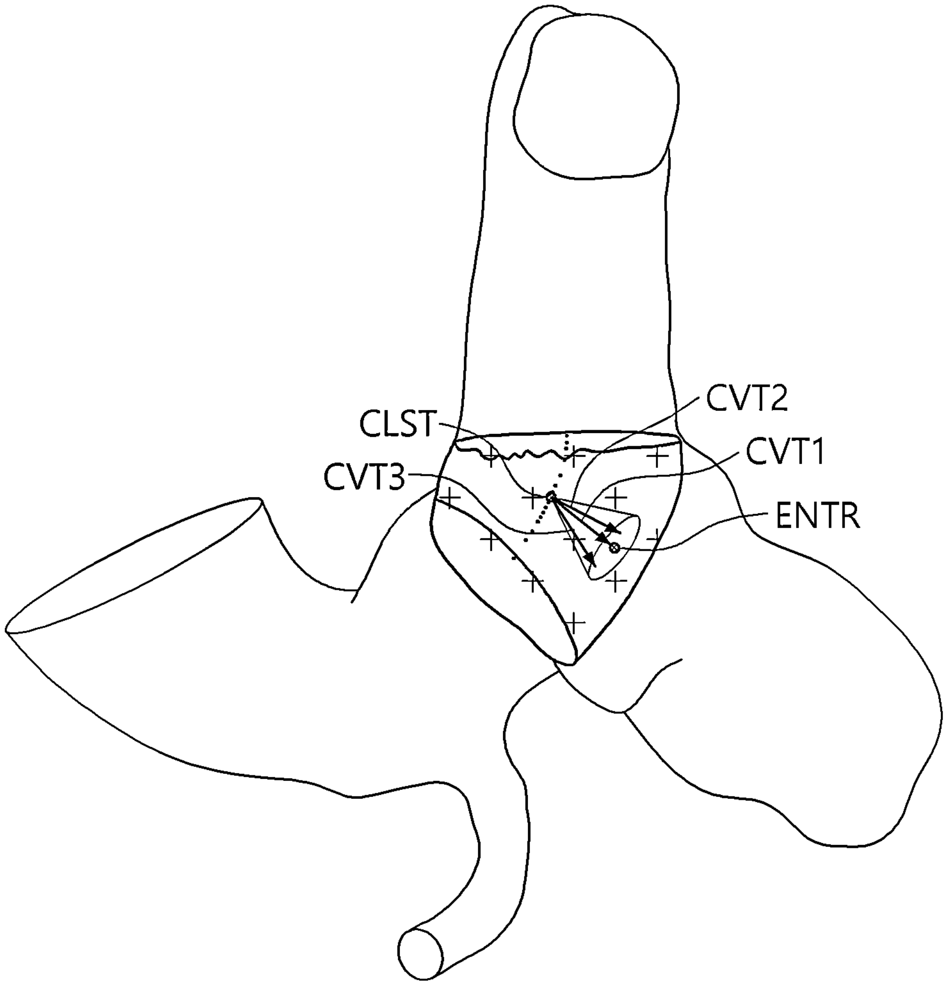
Figure 16:
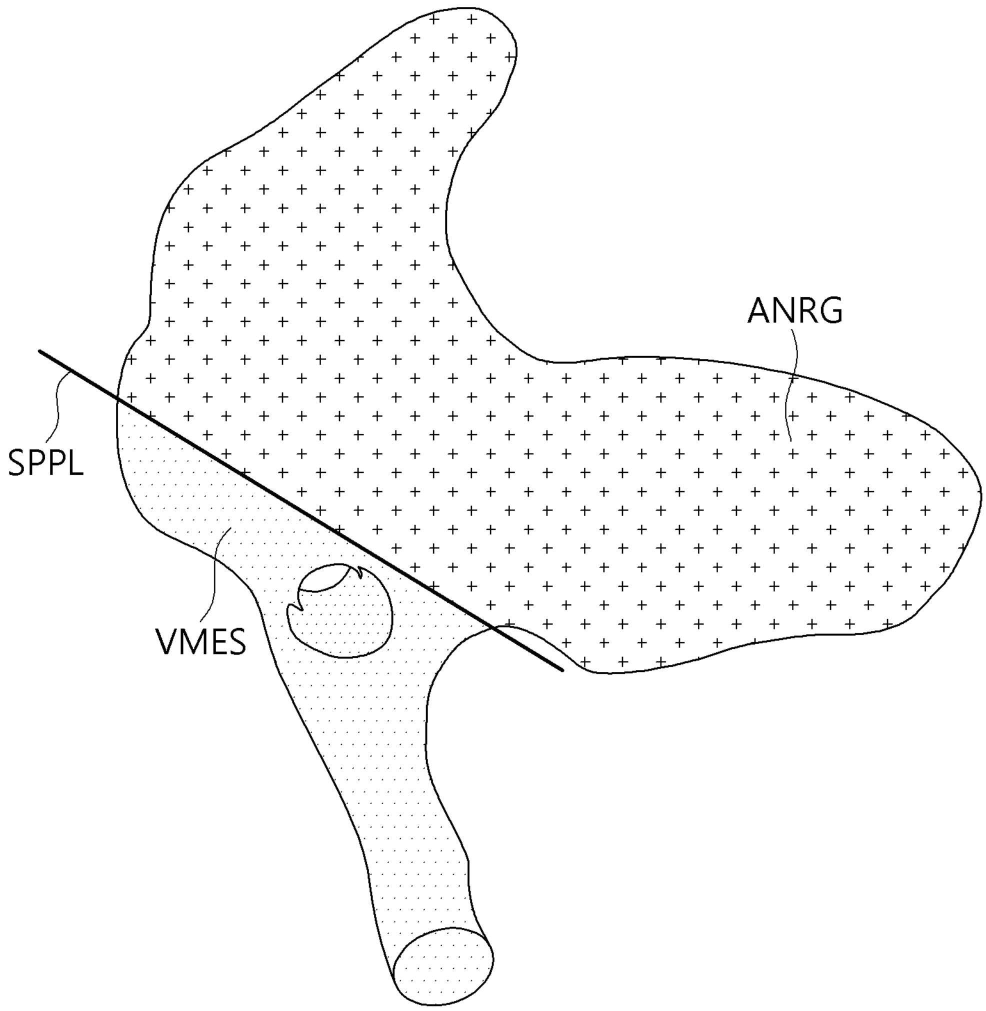

FIG. 13 is a flowchart illustrating a method for generating a separating plane according to an embodiment, and FIGS. 14 to 16 illustrate a method for generating a separating plane by an electronic device according to an embodiment.

Referring to FIG. 13, an electronic device (e.g., 200 in FIG. 1) according to an embodiment may determine a candidate point (S131). To obtain the aneurysm region, a separating plane must be determined. In some embodiments, the separating plane may be defined by a point and a vector. However, the embodiment is not limited thereto. The candidate point may be a candidate for determining the separating plane.

Referring to FIGS. 13 and 14, in some embodiments, the electronic device may define internal points within the parent artery mesh (PRAR) based on a plurality of interpolation points (SPLN) (or an interpolation centerline) and an entry point (ENTR). The electronic device may determine each internal point as the candidate point.

For example, the electronic device may determine a point (CLST) closest to the entry point (ENTR) among the plurality of interpolation points (SPLN). The electronic device may determine the internal points based on points along a line segment connecting the point (CLST) and the entry point (ENTR). For example, the electronic device may determine, as internal points, points on the line segment connecting the point (CLST) and the entry point (ENTR) that are within a reference distance from the entry point (ENTR). In FIG. 14, a first internal point (IPT) is shown as an example of the internal points.

In some embodiments, the electronic device may determine each surface point of the parent artery mesh (PRAR) as a candidate point. The parent artery mesh (PRAR) is composed of a three-dimensional surface, which may include a plurality of cells. For example, a cell is a two-dimensional plane formed by using three surface points, where the surface points represent external points, and they may serve as candidate points for determining the separating plane. In FIG. 14, a first external point (SPT) is shown as an example of the external points.

In some embodiments, the electronic device may determine a first vector that starts from the point (CLST) and ends at the entry point (ENTR). The electronic device may determine a plurality of vectors defined by the point (CLST) and first surface points of the parent artery mesh (PRAR). The electronic device may determine second vectors, among the plurality of the vectors, having an angle with the first vector that is less than or equal to a predetermined angle. The electronic device may determine second surface points, among the first surface points, corresponding to the second vectors as the external points. For example, the predetermined angle may be set to 90 degrees. In this case, the external points would be second surface points, among the first surface points of the parent artery mesh (PRAR), not located behind the point (CLST) in the direction from the point (CLST) toward the entry point (ENTR).

The electronic device may determine a candidate vector (S132). The candidate vector may be a candidate for determining the separating plane. The electronic device may determine the candidate vector based on the first vector.

Referring to FIGS. 13 to 15, the electronic device may determine a first vector (CVT1) that starts from the point (CLST) and ends at the entry point (ENTR). The electronic device may also determine at least one second vectors (CVT2, CVT3) that forms an angle with the first vector (CVT1) that is less than or equal to a reference angle. For example, the electronic device may define a cone using the first vector (CVT1) as the rotation axis and determine a plurality of second vectors (CVT2, CVT3) within the cone. The cone may be a three-dimensional shape obtained by rotating a triangle, which has the reference angle as the angle between its hypotenuse and the rotation axis, around the first vector (CVT1). The electronic device may determine the first vector (CVT1) and at least one second vectors (CVT2, CVT3) as candidate vectors.

The electronic device may determine a candidate plane based on the candidate point and the candidate vector (S133). The candidate plane may refer to a candidate for determining the separating plane. For example, the electronic device may determine, as the candidate plane, a plane that passes through the candidate point and has the candidate vector as its normal vector. The electronic device may determine the candidate plane based on one of the internal points (e.g., IPT) or external points (e.g., SPT), and one of the candidate vectors (e.g., one of CVT1 to CVT3).

The electronic device may calculate the score of the candidate plane. For example, the electronic device may calculate the score based on at least one of a first volume of an aneurysm region, a second volume of a parent artery region, and the perimeter of the intersection line between the separating plane and the vessel mesh. The first volume of the aneurysm region may refer to the volume of the area obtained by the vessel mesh and the separating plane. The second volume of the parent artery region may refer to the volume of the area obtained by a parent artery mesh, clipping points, and the separating plane.

In some embodiments, the electronic device may calculate the score of the candidate plane based on Equation 1.

$$SCR_{CP1} = V1 * w + V2 * (1 - w) \quad \text{[Equation 1]}$$

Herein, $SCR_{CP1}$ may indicate the score of a first candidate plane (CP1), V1 may indicate a first volume, w may indicate a weight, and V2 may indicate a second volume.

In some embodiments, the electronic device may calculate the score of the candidate plane based on Equation 2.

$$SCR_{CP1} = V1 * w_1 + V2 * w_2 \quad \text{[Equation 2]}$$

Herein, $SCR_{CP1}$ may indicate the score of a first candidate plane (CP1), V1 may indicate a first volume, $w_1$ may indicate a first weight, V2 may indicate a second volume, and $w_2$ may indicate a second weight.

In some embodiments, the electronic device may calculate the score of the candidate plane based on Equation 3 or Equation 4.

$$SCR_{CP1} = V1 * w + V2 * (1 - w) - CCF \quad \text{[Equation 3]}$$

$$SCR_{CP1} = \frac{V1 * w + V2 * (1 - w)}{CCF} \quad \text{[Equation 4]}$$

Herein, $SCR_{CP1}$ may indicate the score of a first candidate plane (CP1), V1 may indicate a first volume, w may indicate a weight, V2 may indicate a second volume, and CCF may indicate the perimeter of the intersection line between the first candidate plane (CP1) and the vessel mesh.

However, the embodiment is not necessarily limited to the examples mentioned above. The electronic device may calculate the score using at least one of the first volume, the second volume, and the perimeter, along with various weights.

The electronic device may determine whether the score of the candidate plane exceeds a threshold (S134). The threshold may be a value preset by the user. In some embodiments, the signs of the right-hand terms in the aforementioned Equations 1 to 4 may be reversed. In this case, the electronic device may determine whether the calculated score is below the threshold.

The electronic device may determine the candidate plane as the separating plane to obtain the aneurysm region if the score of the candidate plane exceeds the threshold (S135). Referring to FIG. 16 together, the electronic device may use a separating plane (SPPL) to divide the vessel mesh (VMES) and obtain an aneurysm region (ANRG).

In some embodiments, the electronic device may calculate the scores of all candidate planes generated based on the candidate point and the candidate vectors, and determine candidate plane with the highest score as the separating plane (SPPL).

The electronic device, once the aneurysm region (ANRG) is obtained, may perform a quantitative analysis of the aneurysm region (ANRG). For example, the electronic device may determine parameters such as maximal neck diameter, minimal neck diameter, height, width, and angle for the aneurysm region (ANRG). Herein, the maximal neck diameter may indicate the longest line in the neck of the separating plane (SPPL), and the minimal neck diameter may indicate the longest line perpendicular to the maximal neck diameter. The neck of the separating plane (SPPL) may indicate a closed loop defined by the intersection line of the separating plane (SPPL) and the vessel mesh (VMES). The height may include height 1, height 2, and height (ortho). Height 1 may indicate the longest line extending from the center of mass of the separating plane (SPPL) toward the aneurysm region (ANRG), height 2 may indicate the longest line extending from the midpoint of the maximal neck diameter toward the aneurysm region (ANRG), and height (ortho) may indicate the line extending to the point in the aneurysm region (ANRG) that is farthest from the separating plane (SPPL). The width may indicate the longest line perpendicular to each height, and the angle may indicate the angle formed between the separating plane (SPPL) and each height.

If the score of the candidate plane is below the threshold, the electronic device may proceed to step (S131). In other words, the electronic device may re-determine the candidate point.

In FIG. 13, although the steps (S131 to S135) are illustrated as being included in step (S130) of FIG. 2, step (S130) may be modified to include additional steps or to omit certain steps. For example, step (S130) may be implemented to include steps (S131, S132, and S135). In this case, the electronic device may use an artificial neural network trained by using a training dataset with the candidate point and the candidate vector as input data and the separating plane as output data.

Figure 17:
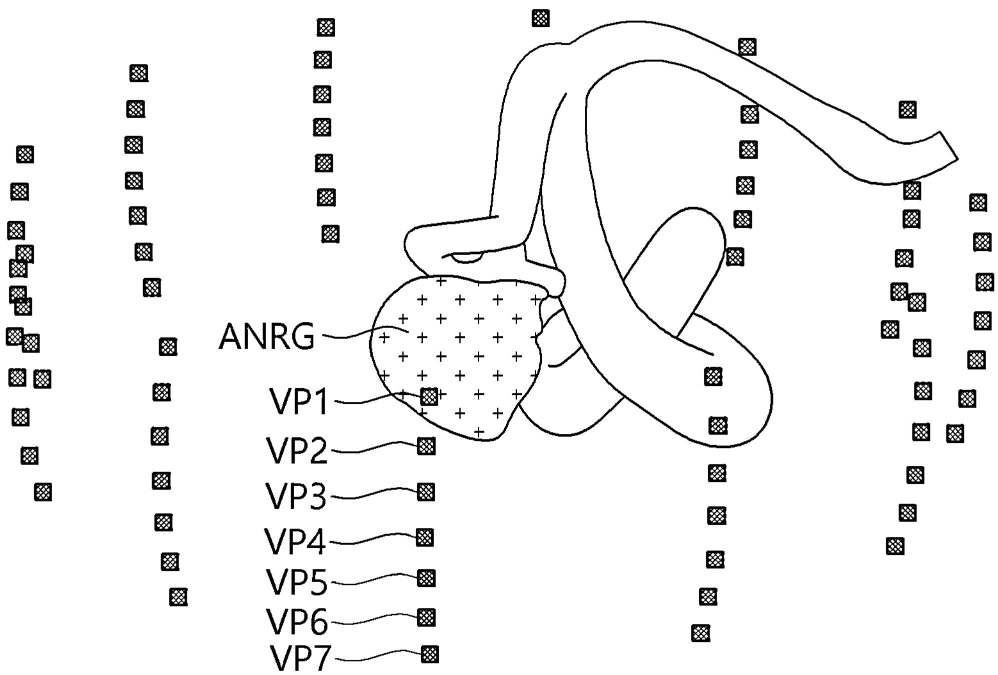
FIG. 17 is a diagram illustrating a method for obtaining a vessel image by an electronic device according to an embodiment.
Figure 18:
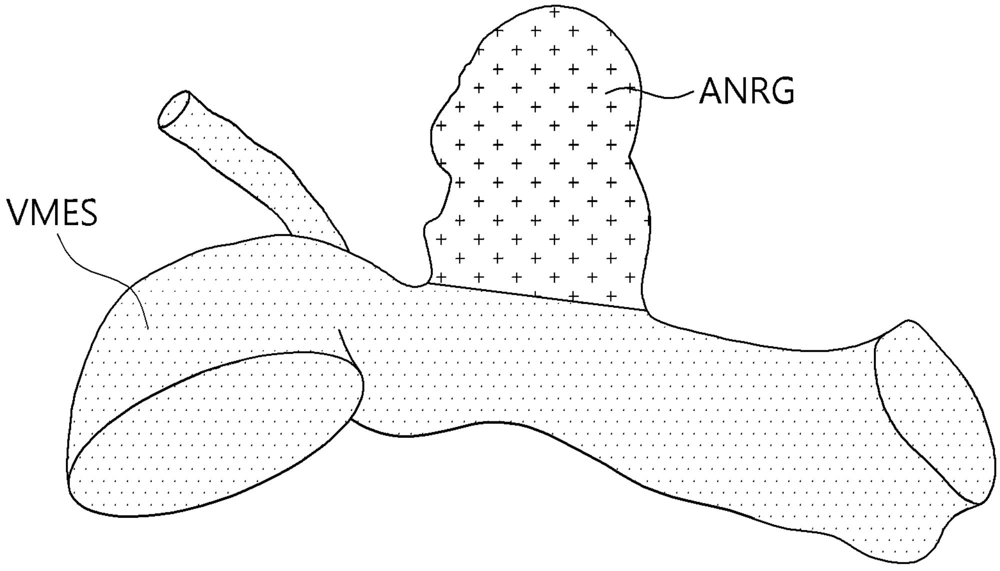
FIG. 18 shows an example of a vessel image obtained by an electronic device according to an embodiment.

FIG. 17 is a diagram illustrating a method for obtaining a vessel image by an electronic device according to an embodiment, and FIG. 18 shows an example of a vessel image obtained by an electronic device according to an embodiment.

Referring to FIG. 17, an imaging device (e.g., 100 in FIG. 1) according to an embodiment may capture images of a first user from various viewpoints (or angles) and transmit the imaging data to an electronic device (e.g., 200 in FIG. 1).

The electronic device may determine the camera viewpoint that best shows the aneurysm region (ANRG) from the received imaging data. The camera viewpoint may indicate positions of the camera captured the imaging data. In FIG. 17, VP1 to VP7 are shown as examples of camera viewpoints determined by the electronic device. The electronic device may determine the camera viewpoints (VP1 to VP7) based on the normal vector of a separating plane (e.g., SPPL in FIG. 16). As the normal vector of the separating plane corresponds to a candidate vector, the electronic device may determine the camera viewpoints (VP1 to VP7) based on the candidate vector (e.g., one of CVT1 to CVT3 in FIG. 15).

In some embodiments, the electronic device may determine the camera viewpoints (VP1 to VP7) such that the angle between a vector pointing from a camera viewpoint to the aneurysm center point (or the aneurysm entry point) and the candidate vector falls within a predetermined angle range. For example, the predetermined angle range may be set with a certain margin around 90 degrees.

In some embodiments, the electronic device may determine a camera viewpoint (VP4) where a vector from the camera viewpoint to the aneurysm center point is orthogonal to the candidate vector. In other words, the electronic device may determine camera viewpoints by including additional viewpoints adjacent to the camera viewpoint (VP4) within a certain margin, such as VP1 to VP3 and VP5 to VP7, or determine camera viewpoints by including fewer viewpoints depending on the desired configuration.

The electronic device may determine the score of the camera viewpoints (VP1 to VP7). The electronic device may determine the score based on the aneurysm region (ANRG). In some embodiments, the electronic device may calculate the score based on the degree of overlap between the aneurysm region (ANRG) and other blood vessels. The electronic device may divide the vessel mesh into the aneurysm region (ANRG) and a blood vessel region by using the separating plane. The electronic device may calculate the area of obscured part of the aneurysm region (ANRG), which is obscured by the blood vessel region (or other blood vessels). The electronic device may determine the score based on the area. In some embodiments, the electronic device may calculate the percentage of the aneurysm region (ANRG) that is obscured by the blood vessel region and determine the score based on the percentage.

In some embodiments, the electronic device may determine the score based on the extent to which the neck of the aneurysm region (ANRG) overlaps with other blood vessels. Specifically, the electronic device may calculate the area of obscured part of the neck of the aneurysm region (ANRG) and determine the score based on this area. The neck of the aneurysm region (ANRG) may be obscured by the blood vessel region.

In some embodiments, the electronic device may determine the score based on how well the neck of the aneurysm region (ANRG) is visible. For example, the electronic device may calculate the score based on the angle between a vector from a camera viewpoint toward the aneurysm center point (or the aneurysm entry point) and the candidate vector of the separating plane. The electronic device may use trigonometric functions (e.g., the sine function) and the angle between these vectors to determine the score.

In other words, the electronic device may assign a relatively high score to a camera viewpoint where the area of the obscured part of the aneurysm region (ANRG) obscured by the blood vessel region is small, the area of the obscured part of the neck of the aneurysm region (ANRG) obscured by the blood vessel region is small, and the angle between the vectors is close to 90 degrees.

In some embodiments, the data captured of the aneurysm region (ANRG) from the camera viewpoint determined by an electronic device according to an embodiment may be as shown in FIG. 18. In FIG. 18, it can be observed that the aneurysm region (ANRG), which is separated from the vessel mesh (VMES), is clearly visible without being obscured by other blood vessels.

While FIG. 17 describes camera viewpoints (VP1 to VP7) as an example, the same explanation applies to other camera viewpoints not specifically referenced by the numbers.

While this invention has been described in connection with what is presently considered to be practical embodiments, it is to be understood that the invention is not limited to the disclosed embodiments. On the contrary, it is intended to cover various modifications and equivalent arrangements included within the spirit and scope of the appended claims.

In some embodiments, each component or a combination of two or more components described with reference to FIG. 1 to FIG. 26 may be implemented with digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry. To provide for interaction with a user, one or more aspects of the disclosure can be implemented on a computer having a display device, e.g., a CRT (cathode ray tube), LCD (liquid crystal display) monitor, LED (light-emitting diode) monitor, OLED (organic LED) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method for generating an aneurysm region, comprising:
- generating a vessel mesh;
- generating a centerline based on the vessel mesh;
- generating a parent artery mesh based on the centerline; and
- generating a separating plane based on the parent artery mesh to obtain the aneurysm region,
- wherein the centerline includes a vessel centerline and an aneurysm centerline, and
- wherein the generating the centerline based on the vessel mesh comprises:
- generating the vessel centerline based on an open vessel of the vessel mesh;
- generating a tube mesh based on the vessel centerline;
- determining an aneurysm center point based on an aneurysm point and the tube mesh; and
- generating the aneurysm centerline based on the open vessel and the aneurysm center point.

2. The method of claim 1, wherein the generating the tube mesh based on the vessel centerline comprises:
- generating the tube mesh based on center points included in the vessel centerline and radius information corresponding to each of the center points.

3. The method of claim 1, wherein the determining the aneurysm center point based on the aneurysm point and the tube mesh comprises:
- generating a plurality of first rays within the vessel mesh, starting from the aneurysm point as a start point;
- determining first points where the plurality of first rays intersect with the tube mesh; and
- determining the aneurysm center point based on the first points.

4. The method of claim 3, wherein the determining the aneurysm center point based on the first points comprises:
- determining a center of the aneurysm point and the first points as a first center point;
- generating a plurality of second rays within the vessel mesh, starting from the first center point as a start point;
- determining second points where the plurality of second rays intersect with the tube mesh; and
- determining the aneurysm center point based on the first center point and the second points.

5. The method of claim 4, wherein the determining the aneurysm center point based on the first center point and the second points comprises:
- determining the center of the first center point and the second points as a second center point; and
- determining the second center point as the aneurysm center point if a distance between the first center point and the second center point is less than a predetermined distance.

6. The method of claim 5, wherein the determining the aneurysm center point based on the first center point and the second points further comprises:

determining a third center point based on the second center point if the distance between the first center point and the second center point is greater than or equal to the predetermined distance; and determining the aneurysm center point based on the distance between the second center point and the third center point.

7. The method of claim 1, wherein the generating the parent artery mesh based on the centerline comprises:

determining an entry point based on the aneurysm centerline and the tube mesh;

dividing the vessel centerline based on the entry point to obtain a first vessel centerline and a second vessel centerline;

determining clipping points indicating a boundary of the aneurysm on each of the first and second vessel centerlines; and generating the parent artery mesh based on the clipping points.

8. The method of claim 7, wherein the determining the entry point based on the aneurysm centerline and the tube mesh comprises:

determining first points where the aneurysm centerline intersects with the tube mesh; and determining the center of the first points as the entry point.

9. The method of claim 7, wherein the determining the clipping points indicating the boundary of the aneurysm on each of the first and second vessel centerlines comprises:

generating a first clipping mesh based on first center points included in the first vessel centerline and radius information corresponding to each of first center points;

determining a first clipping point based on the first center points, the first clipping mesh, and the vessel mesh;

generating a second clipping mesh based on second center points included in the second vessel centerline and radius information corresponding to each of the second center points; and determining a second clipping point based on the second center points, the second clipping mesh, and the vessel mesh.

10. The method of claim 9, wherein the determining the first clipping point based on the first center points, the first clipping mesh, and the vessel mesh comprises:

generating a plurality of first rays, starting from a clipping point candidate of one of the first center points as a start point;

determining first contact points where the plurality of first rays intersect with the first clipping mesh;

determining second contact points where the plurality of first rays intersect with the vessel mesh; and determining the clipping point candidate as the first clipping point based on the first contact points and the second contact points.

11. The method of claim 10, wherein the determining the clipping point candidate as the first clipping point based on the first contact points and the second contact points comprises:

determining the clipping point candidate as the first clipping point if a ratio of a distance from the clipping point candidate to the first contact points to a distance from the clipping point candidate to the second contact points exceeds a threshold.

12. The method of claim 7, wherein the generating the parent artery mesh based on the clipping points comprises:

performing interpolation based on the clipping points to generate an interpolation centerline;

performing interpolation on a first radius information of the clipping points to generate second radius information for the interpolation centerline; and generating the parent artery mesh based on the interpolation centerline and the second radius information.

13. The method of claim 12, wherein the generating the separating plane based on the parent artery mesh to obtain the aneurysm region comprises:

determining one of internal points and external points as a candidate point, wherein the internal points are within the parent artery mesh and are defined based on the interpolation centerline and the entry point, and wherein the external points are on a surface of the parent artery mesh;

determining a candidate vector based on a first vector that starts from a point on the interpolation centerline closest to the entry point and ends at the entry point;

calculating a score of a separating plane candidate determined based on the candidate point and the candidate vector; and determining the separating plane candidate as the separating plane if the score exceeds a threshold.

14. The method of claim 13, wherein the determining one of the internal points and the external points as the candidate point comprises:

determining the internal points based on points along a line segment connecting a point on the interpolation centerline closest to the entry point and the entry point; and determining second surface points as the external points, wherein a plurality of vectors are defined by the point on the interpolation centerline closest to the entry point and first surface points of the parent artery mesh, and wherein the second surface points correspond to second vectors, among the plurality of the vectors, having an angle with the first vector that is less than or equal to a predetermined angle.

15. The method of claim 13, wherein the determining the candidate vector based on the first vector that starts from the point on the interpolation centerline closest to the entry point and ends at the entry point comprises:

determining at least one second vector that forms an angle with the first vector that is less than or equal to a reference angle; and determining the first vector and the at least one second vector as the candidate vector.

16. The method of claim 13, wherein the calculating the score of the separating plane candidate determined based on the candidate point and the candidate vector comprises:

calculating the score based on at least one of a first volume of the aneurysm region obtained by the separating plane, a second volume of a parent artery region obtained by the separating plane, and a perimeter of an intersection line between the separating plane and the vessel mesh.

17. The method of claim 1, wherein the generating the vessel mesh comprises:

obtaining a plurality of imaging data from a plurality of camera viewpoints; and generating the vessel mesh based on the plurality of imaging data, wherein the method further comprises:

generating a plurality of vectors from the plurality of camera viewpoints toward a center point of the aneurysm region;

determining a first vector among the plurality of vectors that forms an angle within a predetermined range with a normal vector of the separating plane;

determining a first viewpoint corresponding to the first vector among the plurality of camera viewpoints; and displaying the aneurysm region based on the first viewpoint.

18. The method of claim 17, wherein the determining the first vector among the plurality of vectors that forms the angle within the predetermined range with the normal vector of the separating plane comprises:

determining second vectors among the plurality of vectors that form an angle within the predetermined range with the normal vector of the separating plane; and determining the first vector among the second vectors based on an area of obscured part of the aneurysm region when displaying the aneurysm region from each viewpoint corresponding to the second vectors, wherein the aneurysm region is obscured by other blood vessels.

19. An electronic device comprising:

a processor; and a memory connected to the processor, wherein the memory is configured to store a program, and the processor is configured to execute the program, and wherein, when the program is executed by the processor, the steps of the method according to claim 1 are implemented.

* * * * *